(12) United States Patent
Nieberding

(10) Patent No.: US 10,391,332 B2
(45) Date of Patent: Aug. 27, 2019

(54) KIT FOR IMMOBILIZATION OF A HUMAN'S BODY PART

(71) Applicant: Reginald Nieberding, Kapellen (BE)

(72) Inventor: Reginald Nieberding, Kapellen (BE)

( * ) Notice: Subject to any disclaimer, the term of this patent is extended or adjusted under 35 U.S.C. 154(b) by 715 days.

(21) Appl. No.: 15/034,681

(22) PCT Filed: Nov. 5, 2014

(86) PCT No.: PCT/EP2014/073766
§ 371 (c)(1),
(2) Date: May 5, 2016

(87) PCT Pub. No.: WO2015/067633
PCT Pub. Date: May 14, 2015

(65) Prior Publication Data
US 2016/0271421 A1 Sep. 22, 2016

(30) Foreign Application Priority Data

Nov. 8, 2013 (EP) .................................... 13192232

(51) Int. Cl.
| | |
|---|---|
| *A61B 90/18* | (2016.01) |
| *A61F 5/37* | (2006.01) |
| *A61N 5/10* | (2006.01) |
| *A61B 90/14* | (2016.01) |
| *A61B 6/04* | (2006.01) |

(52) U.S. Cl.
CPC ................ *A61N 5/10* (2013.01); *A61B 90/14* (2016.02); *A61B 90/18* (2016.02); *A61F 5/3707* (2013.01); *A61N 5/1077* (2013.01); *A61B 6/04* (2013.01); *A61N 2005/1097* (2013.01)

(58) Field of Classification Search
CPC ........... A61B 90/14; A61B 90/18; A61F 5/37; A61F 5/3707; A61N 5/10
USPC ........................................ 128/845, 846, 869
See application file for complete search history.

(56) References Cited

U.S. PATENT DOCUMENTS 5,702,406 A    12/1997 Vilsmeier et al.

FOREIGN PATENT DOCUMENTS

WO    WO 2013/167688    11/2013

OTHER PUBLICATIONS

PCT International Search Report for PCT/EP2014/073766, Form PCT/ISA/210, dated Apr. 2, 2015 (2 pages).

*Primary Examiner* — Keri J Nelson
(74) *Attorney, Agent, or Firm* — Knobbe, Martens, Olson & Bear LLP

(57) ABSTRACT

The present invention provides a kit for immobilization of a patient body part for radiotherapy applications. The kit includes two moldable thermoplastic sheets, a lower sheet for covering the anatomical contours of a first area of the body part and an upper sheet for covering the anatomical contours of a second area of the body part which is not covered by the lower sheet. The upper and lower sheets form a double shell mask enclosing the body part. The sheets may be connected and retained by a fixation device. The sheets have different physical and visual properties.

13 Claims, 3 Drawing Sheets

# KIT FOR IMMOBILIZATION OF A HUMAN'S BODY PART

CROSS-REFERENCE TO RELATED APPLICATIONS

This application is the U.S. National Phase under 35 U.S.C. § 371 of International Application PCT/EP2014/073766, filed Nov. 5, 2014, which claims priority to EP 13192232.0, filed Nov. 8, 2013.

FIELD OF THE INVENTION

The present invention pertains to a kit and a method for immobilizing at least part of a human's body part for receiving radiation treatment. The invention is suitable for use in the medical field, particularly for immobilization purposes in radiotherapy and cancer treatment.

BACKGROUND

The treatment of patients having cancer frequently makes use of radiation therapy wherein radiation is directed to particular sites in the patient's body. These treatments require high precision, reliable and accurate patient set-up to position and immobilize the relevant portion of the patient's body undergoing the radiation. Various devices and equipment are available for effecting such action. For example, patient couches or tables are commonly provided at the radiation machine, e.g., linear accelerator, CT machine, MRI, etc., to support the patient in a prone or supine position while the relevant portion of the patient's body is held in a fixed or immobilized condition. To that end the immobilization of the relevant portion of the patient's body is commonly achieved by various types of devices mounted on the patient couch/treatment table.

A commonly used body part, i.e. the head, restraint device is a mask that is placed over the face of the patient to hold the patient's head stationary. Such masks may be molded to conform to the contours of the patient's face to ensure maximum immobilization. The back of the patient's head and/or contiguous portion of the patient's neck may be supported by a cushion which itself can be pre-contoured for a specific shape or can be conformed, e.g., molded, to the shape of the back of the patient's head. The mask itself can be pre-formed to a shape that will generally conform to the contours of the patient's face, or may be molded on the patient's face to closely conform to those contours. The molding of the mask is typically conducted preceding the first treatment. After this the mask can be mounted on the head of the patient and subsequently will be fixed to the patient support table. However, the patient's head and neck will still have to be supported, such as by cushions filled with granular material, for example, or by preformed cushions. Using cushions, deviations in the position of the head in relation to the preceding treatment can easily occur.

U.S. Pat. No. 5,702,406 discloses a reference system for noninvasive, stereotactic immobilization of a human head in reproducible position. The reference system comprises a head ring having a pair of support legs adapted to be positioned at opposite sides of the head of a specific patient. The reference system also comprises a mask containing a plurality of separate parts capable of assuming a given conformation. A first part is adapted to be conformed to and to cover the anatomical contours of a first area of the specific patient's head. A second part is adapted to be conformed to and to cover the anatomical contours of a second area of the specific patient's head which is not covered by the first part. The reference system further comprises means for connecting the mask parts with one another, said connection means also connecting the connected mask parts to the reference system. Another part of the reference system is a detachable support, made of plastic. The support is used during immobilization for supporting the back of the head of the patient. One of the disadvantages of this system is that the obtained mask has an open area on the cranial side and does not fully cover the head of a patient. Furthermore as mentioned above, the use of support leads to deviations in the position of the head in relation to the preceding treatment.

A disadvantage of the above described system resides in the use of a head support such as a support cushion. The use of said support to shape a mask adapted to a patient's head for instance, results in a mask which is adapted to the pre-shaped form of the support cushion. The obtained mask is hence not fully adapted to the anatomical contours of the body part that needs to be immobilized. In addition, the rotation of said body part will be adapted to the support cushion shape and material. This provides the patient with a very low comfort level especially if the treatment time is long.

Another disadvantage related to the use of a support cushion is the incapacity of the practitioner to be in touch with the body part surface which is supported by the support cushion. Hence, the practitioner will have a limited access to the body part surface supported by the support cushion which leads to a mask which is not fully conform to the anatomical contours of the mentioned body part. In case the practitioner has access to the body part surface which is supported by the support cushion of the prior art, he can ensure a perfect conformity of the mask to the anatomical contours and boney reference structures of the body part that needs to be immobilized. Moreover, the contact of the practitioner with the body part of interest will provide the patient with a security and a comfort feeling.

Still another disadvantage of the immobilization systems described in the prior art is that they comprise several devices that needs to be assembled which, on one hand, represents a high workload for the practitioner and on the other hand, prolongs the time required for the making of the immobilization mask thereby providing the patient with an uncomfortable feeling. The immobilization systems described in the prior art are also very bulky and a high amount of material is required for their manufacture which leads to a non-homogeneous dose delivery and high attenuation of the radiation beam.

The aim of the present invention is to provide a solution to overcome at least part of the above mentioned disadvantages. The invention thereto aims to provide a kit and a method, which are highly effective and easy to use and apply for the immobilization of a patient body part.

SUMMARY

In a first aspect, the present invention provides a kit for immobilization of a patient body part for radiotherapy applications comprising two moldable thermoplastic sheets, a lower sheet for covering the anatomical contours of a first area of said body part and an upper sheet for covering the anatomical contours of a second area of said body part which is not covered by the lower moldable thermoplastic sheet, thereby forming a double shell mask enclosing said body part, the sheets are suitable to be connected and retained by a fixation device; wherein said sheets have different physical properties. The physical properties of the sheets allow the immobilization of body part, using a fixation device, free from any fixation surface, support or cushion.

In a preferred embodiment, the sheets are suitable to be directly molded on the patient's body part thereby obtaining molded sheets. The "double shell" mask obtained by the invention fully covers and encompasses the patient's body part to be immobilized. For instance, for the head, the double shell mask covers the areas corresponding to and including the frontal bone, the parietal bone and the occipital bone while in the prior art system the area corresponding to these bones is only partially covered or is not covered.

The present invention further provides a method for immobilization of a patient body part for radiotherapy applications comprising the steps of: —mounting a heated lower sheet to a fixation device; —placing the patient body part to be immobilized on said lower sheet thereby covering the anatomical contours of a first area of said body part; and—mounting a upper heated sheet to the flanged support member thereby covering the anatomical contours of a second area of said body part which is not covered by the lower sheet; wherein the method is adapted for supporting the immobilized body part free from any fixation surface by the two sheets and the device.

The present invention provides several advantages compared to the kits of the prior art. The invention and more in particular, the physical properties of the moldable thermoplastic sheets, allows the immobilization of a body part without the use of cushion or a support for the body part to be immobilized. Consequently, the sheet will deform according to only and solely the patient's body part shape and anatomical contours. The molded and cured sheets will be exactly adapted and conform to the anatomical contours of the immobilized body part.

The invention does not make use of a material or a support on which the immobilized body part rests, such as cushions, as described in the systems of the prior art. Consequently, the immobilized body part of the patient is, up to 360°, accessible to the practitioner and/or for radiation application. This means that the practitioner can touch and/or apply radiation to any area of the immobilized body part. This is not offered by the systems of the prior art wherein the area of the immobilized body part resting on a cushion is not accessible to the practitioner, not accessible for applying radiation or specific radiation density needs to be applied to apply radiation through the cushion or support material.

DETAILED DESCRIPTION OF THE INVENTION

Figure 1:
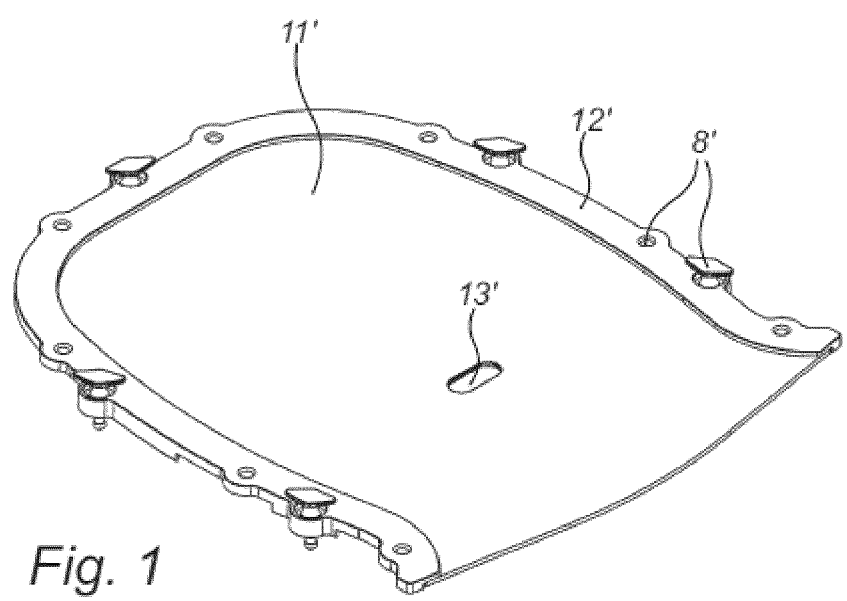
FIG. 1 shows an embodiment of a moldable thermoplastic sheet in initial state according to the present invention. The sheet is connected to a circumferential rim.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight" (weight percent), here and throughout the description unless otherwise defined, refers to the relative weight of the respective component based on the overall weight of the formulation.

The term "initial state" of a thermoplastic sheet used herein refers to a thermoplastic sheet which is still flat, not heated and not molded so not yet deformed. The term "final state" of a thermoplastic sheet used herein refers to a thermoplastic sheet which has been, heated, molded so deformed to conform the anatomical contours of a body portion and cured thereby having a rigid molded thermoplastic sheet.

The term "cured" used herein refers to a thermoplastic sheet that was heated, deformed according to a patient's body part anatomical contours and cooled to ambient temperature such as to rigidify.

The terms "support fixation surface" and "fixation surface" are used herein as synonyms and refer to a surface to which a fixation device is suitable to be mounted and/or fixed. Said fixation surface might be a radiation table for instance.

The present invention relates to a kit and a method for the immobilization of a patient body part. The present invention can be used for the immobilization of any single body part of a human being. The present invention can also be used for the immobilization of more than one body part of a human being, such as the head, the neck and the shoulders and optionally part of the trunk. The present invention is preferably used for the immobilization of a body part for radiotherapy applications. The body part can be the part enclosing any organ of the patient such as the liver, the lungs or the kidneys, such as to deliver radiation to said organ.

In a first aspect, the present invention provides a kit for immobilization of a patient body part for radiotherapy applications comprising two moldable thermoplastic sheets, a lower sheet for covering the anatomical contours of a first area of said body part and an upper sheet for covering the anatomical contours of a second area of said body part which is not covered by the lower moldable thermoplastic sheet, thereby forming a double shell mask enclosing said body part. The sheets are suitable to be connected and retained by a fixation device. Said sheets have different physical.

The immobilization is usually performed on a fixation surface, such as a table, using a fixation device. The lower sheet is the sheet which is proximal to the fixation surface when said body part is immobilized. The upper sheet is the sheet which is distal to the fixation surface when said body part is immobilized. For instance, if a patient's head is to be immobilized and the patient is in the supine position, the lower sheet will cover the rear head of the patient and the upper sheet will cover the front head of the patient. If a patient's head is to be immobilized and the patient is in the prone position, the lower sheet will cover the front head of the patient and the upper sheet will cover the rear head of the patient. The lower sheet is also the first sheet used to achieve the immobilization while the upper sheet is the second sheet that will be used.

The physical property is selected from the group comprising elastic modulus, yield stress, yield strain, strain at break, shore A, tensile strength, tensile modulus, shore D or any combination thereof.

In a preferred embodiment, the sheets have different visual properties. Said properties can be selected from the group comprising: perforations, color, pattern, figures, signs or any combination thereof. Different visual properties provide for easy distinction of the lower sheet from the upper sheet. The sheets can have different colors and/or can be provided with different patterns, figures or signs and/or the at least one of the sheets might be perforated. Preferably the lower sheet is devoid of perforations.

In a preferred embodiment, the sheets have different elasticity. Preferably, before heating and/or molding, the elastic modulus ratio of the lower sheet to the upper sheet is of from 2 to 8, preferably from 3 to 7, more preferably from 4 to 6, most preferably about 5. Through the application, the upper sheet can be referred to by sheet with the highest elasticity or high elastic sheet and lower sheet is referred to by sheet with the lowest elasticity or less elastic sheet.

Preferably, the elastic modulus of the lower sheet before heating and/or molding is of from 1200 to 2200 MPa, preferably from 1300 to 2000 MPa, more preferably from 1400 to 1800 MPa, even more preferably from 1500 to 1700 MPa or any value comprised in the mentioned ranges. Preferably, the elastic modulus of the less elastic sheet is about 1600 MPa.

Preferably, the elastic modulus of the upper sheet before heating and/or molding is of from 100 to 600 MPa, preferably from 150 to 500 MPa, more preferably from 200 to 400 MPa, even more preferably from 250 to 350 MPa or any value comprised in the mentioned ranges. Preferably, the elastic modulus of the upper sheet is about 330 MPa.

In a preferred embodiment, the weight of the lower sheet is at least 15 gr/dm$^3$, preferably at least 18 gr/dm$^3$, more preferably at least 20 gr/dm$^3$, most preferably at least 22 gr/dm$^3$. Said weight is at most 35 gr/dm$^3$, preferably at most 33 gr/dm$^3$, more preferably at most 30 gr/dm$^3$, most preferably at most 25 gr/dm$^3$. The weight of the lower sheet is preferably about 23 gr/dm$^3$, more preferably about 23.25 gr/dm$^3$, most preferably about 23.5 gr/dm$^3$.

Preferably, before heating and/or molding, the yield stress ratio of the lower sheet to the upper sheet is of from 0.5 to 4, preferably from 0.8 to 3, more preferably from 1 to 2, most preferably about 1.5. In a preferred embodiment, the yield stress of the lower sheet before heating and/or molding is from 15 to 35 MPa, preferably from 18 to 32 MPa, more preferably from 20 to 30 MPa, even more preferably from 22 to 28 MPa or any value comprised in the mentioned ranges. The yield stress of the lower sheet is preferably about 25 MPa, preferably about 24 MPa, more preferably about 23 MPa.

In a preferred embodiment, the yield stress of the upper sheet before heating and/or molding is from 10 to 30 MPa, preferably from 12 to 25 MPa, more preferably from 15 to 20 MPa or any value comprised in the mentioned ranges. The yield stress of the upper sheet is preferably about 18 MPa, preferably about 17 MPa, more preferably about 16 MPa.

Preferably, before heating and/or molding, the yield strain ratio of the lower sheet to the upper sheet is of from 0.005 to 0.03, preferably from 0.01 to 0.025, more preferably from 0.015 to 0.02, most preferably about 0.018. In a preferred embodiment, the yield strain of the lower sheet before heating and/or molding is from 0.5 to 8%, preferably from 1 to 7%, more preferably from 1.5 to 6%, even more preferably from 2 to 5% or any value comprised in the mentioned ranges. The yield strain is preferably about 4%, more preferably about 3.5%, most preferably about 3%.

In a preferred embodiment, the yield strain of the upper sheet before heating and/or molding is from 80 to 300%, preferably from 100 to 250%, more preferably from 120 to 220%, even more preferably from 150 to 200% or any value comprised in the mentioned ranges. The yield strain of the upper sheet before heating and/or molding is preferably about 180%.

In a preferred embodiment, the strain at break of the lower sheet before heating and/or molding is from 20 to 30%. In a further preferred embodiment, the strain at break of the lower sheet before molding is from 21 to 29%, preferably from 22 to 28%, more preferably from 23 to 27% or any value comprised in the mentioned ranges. The strain at break is about 24%, preferably about 25%, more preferably about 26%.

In a preferred embodiment, the shore A of the lower sheet before heating and/or molding is at least 85, preferably at least 88, more preferably at least 90, most preferably at least 92. The shore A is at most 100, preferably at most 99, more preferably at most 98, most preferably 97.

The shore A mentioned in this patent application were measured according to the standard Din 53505. The E-modulus, the yield stress, the yield strain and the strain at break mentioned in this patent application were measured as described in ISO 527.

In a preferred embodiment, the shore A of the upper sheet before heating and/or molding is at least 90, preferably at least 91, more preferably at least 92, most preferably at least 94. The shore A is at most 99, preferably at most 98, more preferably at most 97, most preferably 96. Preferably, the shore A is about 94.

In a preferred embodiment, the lower sheet before heating and/or molding has physical properties as defined by the elastic modulus and/or the yield stress and/or the yield strain and/or the strain at break and/or the shore A which are described above or any combination thereof. Preferably, the lower sheet before molding has all the physical properties listed above being: elastic modulus, yield stress, yield strain, strain at break and shore A.

In a preferred embodiment, the upper sheet before heating and/or molding has physical properties as defined by the elastic modulus and/or the yield stress and/or the yield strain and/or the strain at break and/or the shore A which are described above or any combination thereof. Preferably, the upper sheet before molding has all the physical properties listed above being: elastic modulus, yield stress, yield strain, strain at break and shore A.

In a preferred embodiment, the sheet with the lower sheet when heated at 70° C. has at least one or any combination of the following physical properties:
- the elastic modulus is from 0.5 to 10 MPa, preferably from 1 to 8 MPa, more preferably from 2 to 6 MPa, most preferably from 3 to 5 MPa or any value comprised in the mentioned ranges.
- the yield stress is from 3 to 15 MPa, preferably from, 4 to 12 MPa, more preferably from 5 to 10 MPa, most preferably from 6 to 8 MPa or any value comprised in the mentioned ranges. The yield stress is preferably about 7 MPa.
- the yield strain is from 200 to 500%, preferably from 250 to 450%, more preferably from 300 to 400%, most preferably from 350 to 380% or any value comprised in the mentioned ranges. The yield strain is preferably about 360%, more preferably about 370%.
- the strain at break is from 200 to 500%, preferably from 250 to 450%, more preferably from 300 to 400%, most preferably from 350 to 380% or any value comprised in the mentioned ranges. The strain at break is preferably about 360%, more preferably about 370%.

Measurements were not possible to make on the upper sheet heated at 70° C. for one minute.

In a preferred embodiment, the thickness of the lower sheet before molding is of 1.5 to 1.8 mm, preferably about 1.75 mm, more preferably about 0.75 mm. The thickness of the upper sheet before molding, is of 1.5 to 2.5, preferably 2 to 2.4 mm, preferably about 2.3 mm. The thickness of the sheet in its initial state is also called pre-molding thickness. The thickness of the sheet in its final state is also called post-molding thickness.

In a preferred embodiment, in their final state, so after being molded and cured, the thickness of the lower sheet and the thickness of the upper sheet are very close to each other and preferably equal to each other. The post molding thickness is of from 1.4 to 1.9 mm, preferably of from 1.5 to 1.8 mm. The equal post molding thickness of the sheets is advantageous as it provides for a uniform radiation level independently from the position at which said radiations are applied. This means that the inhibition of the radiation by the sheets will be uniform through the double shell mask.

In a preferred embodiment, the upper sheet has a tensile strength of from 2 MPa to 20 MPa, thereby showing a minimum risk of tearing apart in normal circumstances of manual molding. These sheets show improved moldability and may be molded in such a way that they fit more closely to the anatomic shape of the body part to be immobilized than could be achieved up to now, without losing comfort. Preferably, the ultimate tensile strength of the upper thermoplastic sheet is from 2 to 15 MPa. The tensile strength is measured according to ASTM 683 method.

In a preferred embodiment, the flexural modulus of the upper sheet is of from 5 to 37 MPa, more preferably from 7 to 35 MPa as determined with ASTM method D790.

In a preferred embodiment, the cured upper sheet has a shore D hardness which is at least twice the shore D hardness of the upper sheet at the initial state. Preferably the shore D hardness of the cured upper sheet is 40-60; preferably around 55.

In a preferred embodiment, the upper sheet has a melt index which is between 1 and 50 g/10 min, preferably between 2 and 25 g/10 min. With melt index is meant the melt index measured according to ASTM D1238 test method at 190° C., 2.5 kg. The thermoplastic sheet has some, but limited crystallinity. The total crystallinity of the upper sheet is preferably less than 25%, more preferably less than 21%. Herein % of crystallinity is expressed as wt. % of crystalline part of thermoplastic sheet with respect to the total weight of thermoplastic sheet.

In a preferred embodiment, the melt temperature $T_m$ of the lower and/or the upper sheet is in the range of from 50 to 85° C., preferably from 65 to 75° C., more preferably about 70° C. In a preferred embodiment, the crystallization temperature $T_c$ of the lower and/or the upper sheet is in the range of from 19 to 25° C.

The upper sheet can be perforated or non-perforated. In a preferred embodiment, the upper sheet is perforated. The perforations diameter is comprised between 0.1 mm and 3 mm and preferably between 0.5 and 2 mm, more preferably between 1 to 1.3 mm. Said perforations may be positioned in rows separated by 1 mm to 5 mm. The perforations may represent 10% to 90%, preferably 20% to 80%, more preferably 30% to 70% of the sheet surface. The perforations allow the skin of the patient to breathe even after application of the thermoplastic sheets. In a preferred embodiment, the lower sheet is devoid of perforations.

In a preferred embodiment, each moldable sheet is suitable to be dismountably coupled to a circumferential rim having a number of connection means for connecting the sheets to a fixation device.

Figure 1A:
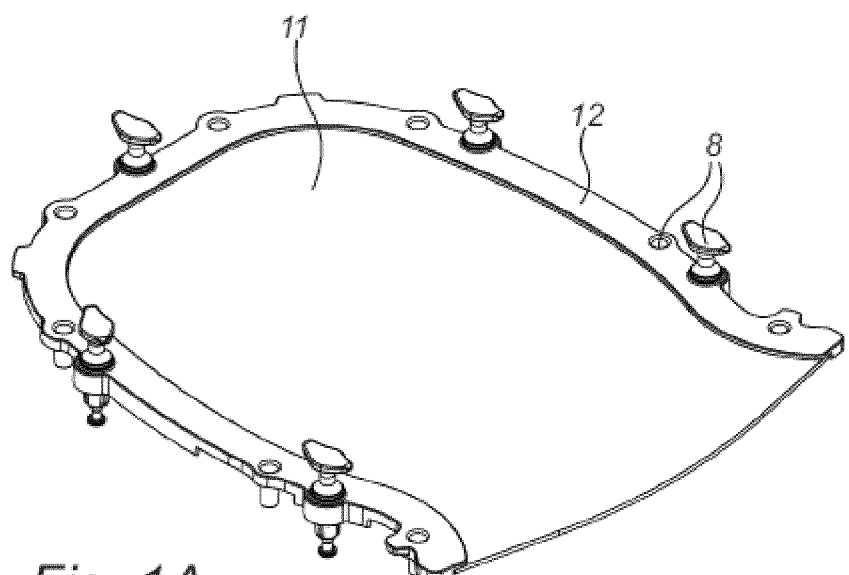
FIG. 1A shows an embodiment of the moldable thermoplastic sheet of FIG. 1. The sheet is devoid of opening.

FIG. 1 shows a moldable thermoplastic sheet 11' according to an embodiment of the present invention. The moldable thermoplastic sheet is in its initial state and is connected to circumferential rim 12' provided with attachment means 8'. The moldable thermoplastic sheet 11' comprises an opening 13' which can correspond to the nose or to the mouth of the patient's when the sheet is cured. The thermoplastic sheet may be provided with more than one opening. FIG. 1A shows another embodiment of the moldable thermoplastic sheet 11 wherein the sheet is devoid of any opening.

In a preferred embodiment, the thermoplastic sheets 11, 11' and the circumferential rims 12, 12' are physically (i.e. heat bonding), mechanically (i.e. clamping), chemically bonded (i.e. glued) or ultrasound bounded to each other. In another preferred embodiment, the thermoplastic sheet 11, 11' and the circumferential rim 12, 12' are dismountably fixed to each other, via snap-fit system.

In a preferred embodiment, the connection means 8 of the circumferential rim 12 of the lower thermoplastic sheet 11 are positioned such as to correspond or superimpose with the connection means 8' of the circumferential rim 12' of the upper thermoplastic sheet 11' and/or to attachment means provided in the fixation device. In a preferred embodiment, the circumferential rims 12, 12' of the lower sheet and of the upper sheet are designed to be superimposable (FIG. 1 and FIG. 1A).

When immobilized, the body part is contained in the double shell mask which is then in contact only with the circumferential rims and the fixation device.

In a preferred embodiment, when the sheets are to be molded, the sheet with the lowest elasticity is warmed by immersion in an aqueous liquid having a temperature comprised between 70-90° C. Preferably said sheet is immersed for 1 second. The warmed sheet attached to the device is now suitable for being molded by placing a body part on the sheet. The warmed sheet will deform according to the contours of a first area of said body part. The deformed sheet will not come in contact with the fixation device and/or the fixation surface.

In a preferred embodiment, at least one and preferably both thermoplastic sheets show reduced draping when warmed. Gamma irradiation can be applied or can be not applied to the thermoplastic sheets of the invention. The thermoplastic sheets can be coated or non-coated. A polyurethane polymer coating can be applied on the thermoplastic sheets.

In a preferred embodiment, at least one and preferably both thermoplastic sheet are optically transparent. The optical transparency permits using positioning markers on the body part and/or the sheets to facilitate re-positioning. This renders the thermoplastic sheets suitable for use in radiation therapy and diagnostic imaging and any other applications where an accurate re-positioning of the immobilization device is of high importance.

In another preferred embodiment, at least one and preferably both thermoplastic sheets have a softening temperature of less than 60° C., preferably of less than 65° C. and comprises a thermoplastic copolymer of a lactone and a lactide in a weight ratio of from 96:4 to 87:13, respectively, wherein the copolymer has a melt temperature Tm in the range of from 47 to 58° C. In a preferred embodiment, said copolymer of the thermoplastic sheet has a melt temperature Tm in the range of from 50 to 85° C., preferably from 65 to 75° C., more preferably about 70° C. and a crystallisation temperature Tc in the range of from 19 to 25° C.

In a preferred embodiment, the copolymer of the thermoplastic sheet has a molecular weight of at least 30000, and preferably from 40000 to 100000. In another preferred embodiment, the copolymer of the thermoplastic sheet is obtained from a lactone and lactide in a weight ratio of from 93:7 to 91:9.

In a preferred embodiment, the upper and/or the lower thermoplastic sheet of the present invention comprises a core layer having an upper surface and lower surface. The core layer has a thermoplastic composition comprising polycaprolactone and polyurethane. the upper and/or the lower sheets comprise also a first outer layer disposed over the upper surface of the core layer and a second outer layer disposed over the lower surface of the core layer. In a preferred embodiment, the first outer layer comprises a material formed from a yarn comprising polyamide and elastane. In a preferred embodiment, the second outer layer comprises open cell foam. The first and the second outer layers are bonded to the core layer so as to form a single sheet.

In a preferred embodiment, the core layer comprises 20% to 40%, polyurethane, and 60% to 80% (w/w) polycaprolactone. In a preferred embodiment, the core layer further comprises between 1 to 40% (w/w) of non-metallic, heat-accumulating microspheres.

In a preferred embodiment, the yarn of the first outer layer comprises between 80% to 95% polyamide, and between 5% and 15% elastane. The thickness of the first outer layer is between 0.05 and 1.5 mm. The fabric weight of the first outer layer is between 210 g/m$^2$ and 230 g/m$^2$.

In a preferred embodiment, the second outer layer is made from polyurethane, polyester polyurethane or polyether open-cell foam.

In a preferred embodiment, the upper and/or the lower thermoplastic sheet comprise an intervening layer disposed between the core layer and the first outer layer, and/or disposed between the core layer and the second outer layer, made from the same material as the core and with higher polycaprolactone content.

In another preferred embodiment, the upper and/or the lower thermoplastic sheet of the present invention comprises a mixture of a polycaprolactone resin with a styrene/acrylonitrile copolymer resin. Preferably, the caprolactone monomer is reacted at 100-230° C. in the presence of a catalyst by using water in the monomer as an initiator to obtain a polycaprolactone resin (A) of a relative viscosity (measured with a capillary viscometer) of 1.50-2.80. Separately, a styrene monomer is copolymerized with 20-35 wt % acrylonitrile monomer to obtain a styrene/acrylonitrile copolymer resin (B). Component A is mixed with component B at a weight ratio of 50-95/50-5, and the resulting mixture is optionally mixed with a metal salt of a higher fatty acid (e.g., calcium stearate).

In a preferred embodiment, when cured, at least one and preferably both thermoplastic sheets of the invention show limited shrinking and are soft such as to provide comfort to the patient. In a preferred embodiment, when cured, at least one and preferably both thermoplastic sheets are rigid and have a memory effect that, after heating, return to the shape formed on cooling. The sheets are non-elastic in the hardened condition. The anatomical shaped medical articles obtained from thermoplastic sheets of the prior art and/or available on the market deform and return to the layer or flat status when they are subject to heat treatment. This is not the case of the thermoplastic sheets of the present invention which are characterized by a memory effect. Said memory effect is very advantageous as it avoids deformation and/or a return to the layer or flat status of the hardened thermoplastic sheets after certain treatments, such as sterilization and/or washing at high temperatures (from 85 to 100° C.).

In a preferred embodiment, the thermoplastic sheets are directly moldable on the human body and present the advantage that it they are unbreakable in case of hard handling or after falling. Moreover, the thermoplastic sheets are preferably optically transparent which gives the possibility to observe whether or not it has been properly molded to the body part. The thermoplastic sheets can also be semi-transparent or opaque.

Preferably, the sheets according to any embodiment of the invention are treated with an antibacterial product before being used. In a further preferred embodiment, said sheets comprise at least one antibacterial compound or a mixture of antibacterial compounds. Further, the sheets are not susceptible to any crimping during use or storage.

The sheets of the present invention are suitable to be used for the immobilization of any patient's body part. Said patient can be in the prone position or in the supine position.

In a second aspect, the present invention further provides a method for immobilization of a patient body part for radiotherapy applications comprising the steps of:
heating and mounting a lower moldable thermoplastic sheet to a fixation device;
placing the patient body part to be immobilized on said lower heated moldable thermoplastic sheet such as to deform the lower moldable thermoplastic sheet into a shape which is conform to the anatomical contours of a first area of the patient body part and in an optimized position for the radiation dose delivery with respect to the critical organs and which covers said first area. If the head of the patient is to be immobilized, the patient lays the back of his head (parietal and occipital bone) into the lower heated thermoplastic sheet. The lower thermoplastic sheet will conform to the anatomical contours of the back of the patient's head and the desired position and rotation in the XZ and YZ plane,
cooling the lower moldable thermoplastic sheet to ambient temperature to rigidify the deformed lower moldable thermoplastic sheet. The cured thermoplastic sheet will have the same shape as the back or the front head of the patient, Heating and mounting an upper moldable thermoplastic sheet to the same fixation device such as to deform said upper sheet into a shape which is conform and covers the anatomical contours of a second area of the patient body part which is not covered by the first sheet. If the lower thermoplastic sheet was used to conform to the anatomical contours of the back of the head, then the upper sheet will be used to conform to the front of the head (the patient's face or front head), cooling the upper sheet to ambient temperature to rigidify the deformed upper sheet. The patient remains in the same position during the production of the double shell mask. This means that, for mounting the upper thermoplastic sheet, the patient is maintained in the same position as for mounting the lower thermoplastic sheet, wherein the upper sheet and the lower sheet have different physical and visual properties. The method is adapted for supporting the immobilized body part free from any fixation surface using the two sheets and the fixation device. Free from any fixation surface refers to the fact that the immobilized body part is not in contact with any fixation surface but is separated from said surface by a free space.

In a preferred embodiment, the sheets as described above are used in the method of the invention.

In a preferred embodiment, a pressure is applied on the body part to be immobilized such as to conform the lower sheet and/or the upper sheet to the anatomical contours of said body part. In a preferred embodiment, the upper heated moldable thermoplastic sheet is brought in contact with the patient's body part without pressing it against said body part. The upper sheet is provided with high elasticity such as it conforms the patient's body part anatomical contours without pressure requirement. In some cases and wherein the face is covered by the upper sheet, it might be required to apply a pressure on the bone of the nose to conform the sheet to the nose of the patient.

The cured lower and upper thermoplastic sheets form an immobilization double shell mask covering the entire body part of the patient. The double shell mask is personalized to the patient's head anatomy.

In a preferred embodiment, when mounted on a fixation device, the lower moldable thermoplastic sheet is not supported in its central region or in any point by a cushion for instance but is only circumferentially supported by the rims. This is achievable as the lower thermoplastic sheet has a rigidity that allows providing a sufficient force to support the rear or the front head or body part and simultaneously providing a sufficient elasticity such as to deform the sheet according to the anatomical contours of the rear or the front head or body part. After cooling, the cured lower thermoplastic sheet will be separated from the fixation surface by an open accessible space. Said open accessible space is created underneath the cured lower thermoplastic sheet. This is advantageous as the thermoplastic sheet will deform according to only and solely the patient's head shape. In addition, the practitioner will have access and will be able to touch, support and shape the thermoplastic sheet when the patient's head is placed on the other surface of the sheet. The practitioner can than make sure that the sheet is perfectly matching the anatomical contours of the head.

In a preferred embodiment, the upper and the lower moldable thermoplastic sheets are heated at a temperature comprised between 70 and 90° C., preferably between 65 and 85° C. The sheets may be softened by warming them to a temperature above their glass transition temperature, for instance by immersion in warm water, at which temperature they becomes shapeable. In a preferred embodiment, the sheets are warmed by immersion in an aqueous liquid having a temperature comprised between 70-90° C. Preferably the sheets are immersed for at least 1 second, preferably at least 2 seconds, more preferably at least 3 seconds and at most for 8 seconds, preferably at most 7 seconds, more preferably at most 6 seconds. As described above, the sheets are allowed to cool below their glass transition temperature, preferably to ambient temperature of 20° C. to 30° C. The sheets will rigidify and provide a form-fitting double shell mask.

Although warming of the thermoplastic sheets will cause the sheets to become stretchable and deformable, they can be transported without damage by taking hold of the circumferential rims of the sheets. Said circumferential rims can be permanently fixed to the moldable thermoplastic sheets or can be dismountably fixed to said sheets. The latter configuration is advantageous as it allows optimizing the cleaning of the sheets both in their initial and final state. Furthermore, dismountable circumferential rims can be easily changed by new rims if required, for instance if the rim is damaged.

Figure 2:
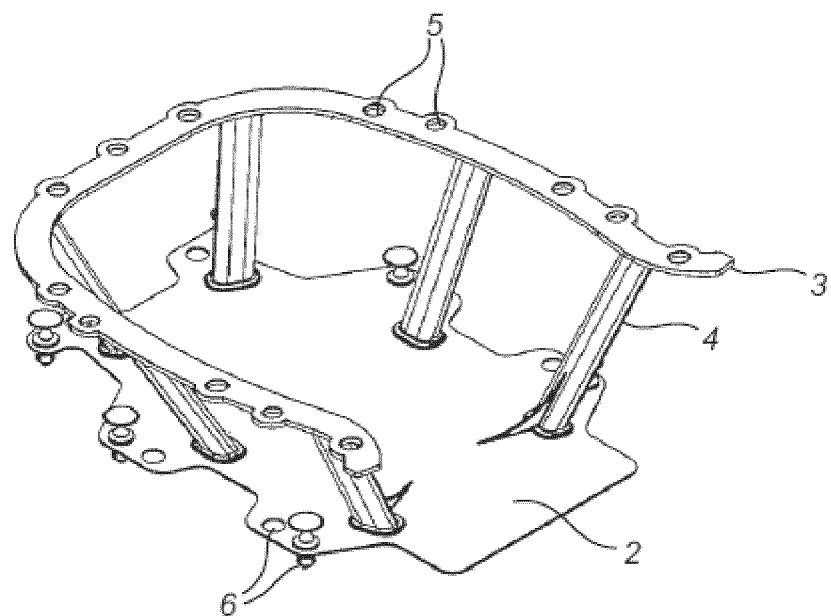
FIG. 2 shows a fixation device to which the sheets according to an embodiment of the invention are suitable to be attached.

In a preferred embodiment, the sheets of the present invention are suitable to be connected and retained by a fixation device. Said device can be any device suitable for immobilization of a patient body part and suitable for the attachment of the sheets of the invention and/or the circumferential rims of the sheets. The fixation device might be provided with at least one flanged support member 3 suitable to receive and retain said two sheets (FIG. 2).

Preferably, the flanged support member 3 is suitable to be mounted on a fixation surface, such as table, using support member fixation means 4, such as said flanged support member is mounted and at a distance d from said fixation surface. In a preferred embodiment, the flanged support member is mounted substantially parallel to the fixation surface. Preferably, the flanged support member is mounted such as to be contained in a plane which is substantially parallel to the plane of the fixation surface.

The fixation device might comprise a bottom plate 2 which can permanently or dismountably connected to said flanged support member 3 by the flanged support member fixation means 4. The bottom plate can be provided with fixation means 6 for mounting said bottom plate to a fixation surface.

In a preferred embodiment, the at least one flanged support member 3 comprises a plurality of attachment means 5 adapted to receive at least two sheets or two moldable thermoplastic sheets, for instance the sheets according to the present invention.

In a preferred embodiment, the connection means 8 of the circumferential rim 12 of the lower sheet 11 are positioned such as to correspond to all or to a part the connection means 8' of the circumferential rim 12' of the upper sheet or upper thermoplastic sheet and/or to all or to a part of the attachment means 5 of the flanged support member 3 of the device 1 when the lower and the upper sheets or thermoplastic sheets are simultaneously attached to the flanged support member 3.

Figure 3:
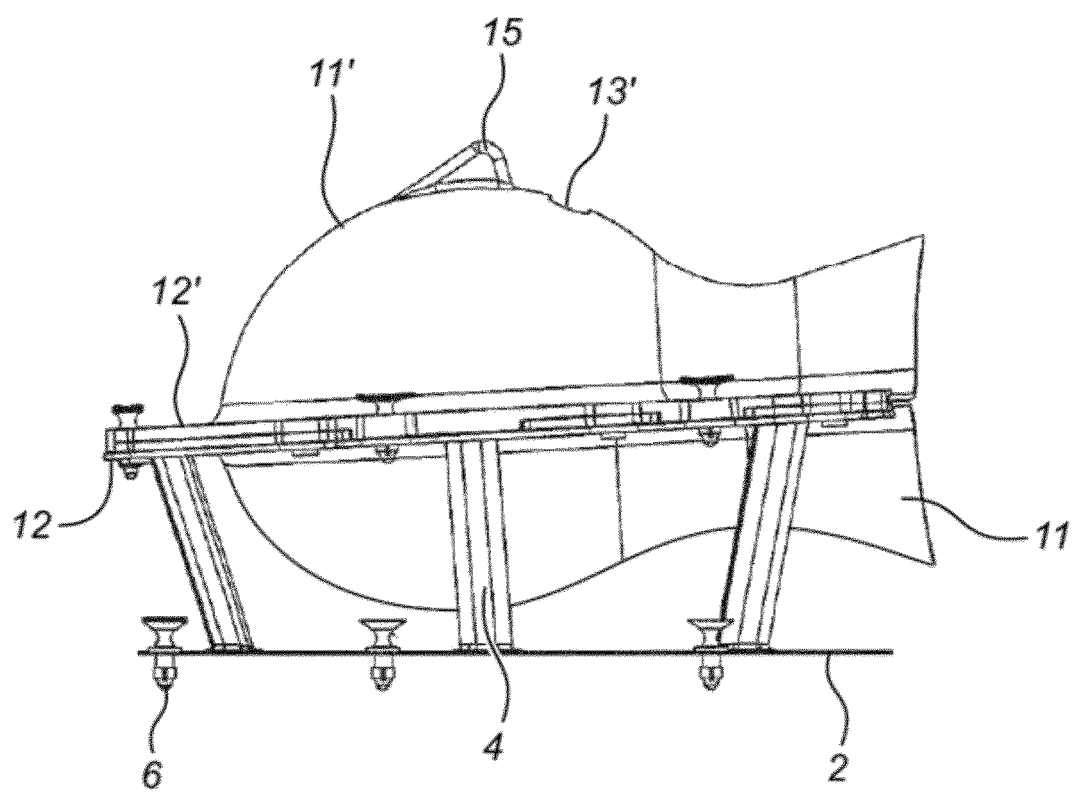
FIG. 3 shows a side view of an immobilization device on which the sheets of the invention are fixed and retained for the immobilization of the patient's head.

FIG. 3 shows a side view of an immobilization device to which the sheets of the present invention are fixed and molded for the immobilization of a patient's head. The assembly comprises the device as described above and the cured thermoplastic sheets 11, 11'. The entire head is covered by the double shell mask of the present invention. The cured upper thermoplastic sheet 11' presents a protrusion 15 corresponding to the nose of the patient and is provided with an opening 13' corresponding to the mouth of the patient The sheets of the invention can be adapted to the immobilization of any body part or more. For instance, the sheets can be adapted for immobilizing the head and the neck and at least partially the trunk of a patient.

The patient's body part immobilized using the kit and/or method according to any embodiment of the present invention is immobilized in a free floating manner. This refers to the fact that said body part is only supported by the thermoplastic sheet and the flanged support member. The body part is immobilized in a way which is devoid of any support cushion or support material. A free space is hence available between the immobilized body part and the fixation surface of the device thereby providing a 360° C. free access of the practitioner and/or the radiotherapy radiation to the immobilized body part. The absence of cushion or support material makes it possible to use any radiation density. In the prior art systems and/or methods wherein a cushion or a support material is used, the radiation should have a specific density in order to penetrate said cushion or support material thereby reaching a specific region of the immobilized body part.

EXAMPLE

The properties of the lower sheet and the upper sheet according to the present invention were compared to the properties of a sheet of the prior art. The properties were measured on non-heated sheets, so measurements were made on the sheets before molding. The properties were also measured on the sheets heated at 70° C. for 1 minute. The heating was performed by placing the sheets in a 70° C. water bath for 1 minute. The results are shown in tables 1, 2 and 3. The measured properties are the elastic modulus, the yield stress, the yield strain, the strain at break and the shore A.

The shore A was measured according to the standard Din 53505. The E-modulus, the yield stress, the yield strain and the strain at break were measured as described in ISO 527.

TABLE 1 properties of the lower sheet according to the invention

|  | Non-heated | | | Heated at 70° C. for 1 min | | |
|---|---|---|---|---|---|---|
|  | Measurement number | | | | | |
|  | 1 | 2 | 3 | 1 | 2 | 3 |
| Elastic modulus (MPa) | 1570 | 1640 | 1620 | 4 | 4.8 | 4 |
| Yield stress (MPa) | 23.3 | 24.4 | 23.3 | 7.38 | 7.05 | 7.58 |
| Yield strain (%) | 3.4 | 3.3 | 3.4 | 320 | 360 | 440 |
| Strain at break (%) | 26 | 25 | 28 | 320 | 360 | 440 |
| Shore A |  | 98 |  |  | 98 |  |

TABLE 2 properties of a sheet of the prior art.

|  | Non-heated | | | Heated at 70° C. for 1 min | | |
|---|---|---|---|---|---|---|
|  | Measurement number | | | | | |
|  | 1 | 2 | 3 | 1 | 2 | 3 |
| Elastic modulus (MPa) | 250 | 348 | 300 | NM | NM | NM |
| Yield stress (MPa) | 19.7 | 18.3 | 18.7 | NM | NM | NM |
| Yield strain (%) | 590 | 600 | 600 | NM | NM | NM |
| Strain at break (%) | NB | NB | NB | NM | NM | NM |
| Shore A |  | 97 |  |  | 97 |  |

NB = no break
NM = not measurable

TABLE 3 properties of the upper sheet according to the invention

|  | Non-heated | | | Heated at 70° C. for 1 min | | |
|---|---|---|---|---|---|---|
|  | Measurement number | | | | | |
|  | 1 | 2 | 3 | 1 | 2 | 3 |
| Elastic modulus (MPa) | 336 | 315 | 345 | — | — | — |
| Yield stress (MPa) | 16.6 | 16.8 | 16.3 | — | — | — |
| Yield strain (%) | 180 | 180 | 180 | — | — | — |
| Strain at break (%) | NB | NB | NB | — | — | — |
| Shore A |  | 94 |  |  | 94 |  |

As can be seen from the tables above, the sheets of the present invention have different properties compared to the sheet of the prior art which shows the highest yield strain before heating and/or molding. The lower sheet of the present invention has an elastic modulus which is higher than the upper sheet and the sheet of the prior art. The system and the properties of the sheets of the present invention provide for the immobilization of the patient's body part free from the fixation surface and/or from any cushion or support material.

It is to be understood that the features described for an embodiment of the present invention are suitable to be applied to any other described embodiment of the invention without departing from the scope of this invention which is defined by the appended claims.

Although the present invention has been described with reference to preferred embodiments thereof, many modifications and alternations may be made by a person having ordinary skill in the art without departing from the scope of this invention which is defined by the appended claims.

What is claimed is:

1. A kit for immobilization of a patient body part for radiotherapy applications comprising two moldable thermoplastic sheets, a lower sheet for covering the anatomical contours of a first area of said body part and an upper sheet for covering the anatomical contours of a second area of said body part which is not covered by the lower sheet thereby forming a double shell mask enclosing said body part, wherein the sheets are configured to be connected and retained by a fixation device; and wherein said sheets have different physical properties and wherein the yield strain ratio of the lower sheet to the upper sheet is from 0.005 to 0.03.

2. The kit according to claim 1, wherein the elastic modulus ratio of the lower sheet to the upper sheet is from 2 to 8.

3. The kit according to claim 1, wherein the elastic modulus of the lower sheet before molding is from 1200 to 2200 MPa.

4. The kit according to claim 1, wherein the yield stress ratio of the lower sheet to the upper sheet is from 0.5 to 4.

5. The kit according to claim 1, wherein the yield stress of the lower sheet before molding is from 15 to 35 MPa.

6. The kit according to claim 1, wherein the yield strain of the lower sheet before molding is from 0.5 to 8%.

7. The kit according to claim 1, wherein the strain at break of the lower sheet before molding is from 20 to 30%.

8. The kit according to claim 1, wherein the lower sheet is devoid of perforations.

9. The kit according to claim 1, wherein the thickness of the lower sheet before molding is 1.5 to 1.8 mm.

10. The kit according to claim 1, wherein the thickness of the upper sheet is 2 to 2.5 mm.

11. The kit according to claim 1, wherein each sheet is configured to be dismountably coupled to a circumferential rim having a number of connection means for connecting the sheets to the fixation device.

12. The kit according to claim 11, wherein the circumferential rims of the sheets and/or the connection means of said rims are configured to be superimposable.

13. A method for immobilization of a patient body part for radiotherapy applications comprising the steps of:

heating and mounting a lower moldable thermoplastic sheet to a fixation device, placing the patient body part to be immobilized on said lower sheet thereby deforming the sheet into a shape which conforms to the anatomical contours of a first area of the patient body part, cooling the lower sheet to ambient temperature, heating and mounting an upper moldable thermoplastic sheet to the same fixation device thereby deforming said upper sheet into a shape which conforms to and covers the anatomical contours of a second area of the patient body part which is not covered by the first sheet thereby forming a double shell mask enclosing said body part, and cooling the upper sheet to ambient temperature, wherein the upper sheet and the lower sheet have different physical properties and wherein the yield strain ratio of the lower sheet to the upper sheet is from 0.005 to 0.03.

* * * * *